United States Patent [19]

Garner et al.

[11] 4,351,184
[45] Sep. 28, 1982

[54] SURFACE INSPECTION EQUIPMENT

[75] Inventors: Henry C. Garner, Mexborough; Jack Broadbent, Rotherham, both of England

[73] Assignee: British Steel Corporation, England

[21] Appl. No.: 226,639

[22] Filed: Jan. 21, 1981

[30] Foreign Application Priority Data

Feb. 14, 1980 [GB] United Kingdom ................ 8005034

[51] Int. Cl.³ .......................................... G01N 19/08
[52] U.S. Cl. ..................................... 73/104; 73/618; 73/432 R; 324/238
[58] Field of Search ................. 73/105, 104, 618, 620, 73/622, 432 R; 324/232, 238

[56] References Cited

U.S. PATENT DOCUMENTS

| 3,974,442 | 8/1976 | Savidge et al. | 324/37 |
| 4,106,347 | 8/1978 | De Kerlegand | 73/662 |
| 4,314,203 | 2/1982 | Haberlein | 324/238 |

FOREIGN PATENT DOCUMENTS 2008259  5/1979  United Kingdom .

OTHER PUBLICATIONS

Pp. 85–92 Iron and Steel Engineer, Sep. 1970, "Eddy Current Inspection of Semi-Finished Billets-Including Corners".

Primary Examiner—S. Clement Swisher
Attorney, Agent, or Firm—Bacon & Thomas

[57] ABSTRACT

The invention concerns the inspection of the corners of a square or rectangular metal billet. The inspection apparatus includes inspection probes (25) supported from a scanning head mounted between entry and exit boxes (13). The two boxes include ram displaceable rollers (4) which are moved into engagement with the other surfaces of the billet as it passes through the apparatus so positively siting the inspection probes above the corners of the billet. The probes are connected to transmit electrical pulses representative of the condition of the billet corners to signal processing equipment remote from the inspection apparatus.

9 Claims, 4 Drawing Figures

SURFACE INSPECTION EQUIPMENT

The invention relates to surface inspection equipment and particularly, but not exclusively, relates to such equipment for detecting defects in corner surfaces of steel billets.

According to the present invention in one aspect, there is provided apparatus for inspecting a corner surface of an elongate metallic object of generally rectangular or square cross-section comprising a rigid assembly of an entry roller box and a scanning head supported for movement about the path to be taken by an object under inspection, the entry roller box comprising several rollers movable collectively into contact with flat surfaces of an object to be inspected as it enters the entry roller box to locate the assembly positively with respect to the object with a surface inspection probe of the scanning head sited opposite a corner of the object.

The rigid assembly may additionally include an exit roller box similarly comprising several rollers movable collectively into contact with flat surfaces of an object under inspection as it leaves the assembly through the exit box.

Preferably, the scanning head carries a plurality of inspection probes collectively movable to positions immediately above the corners of an object under inspection. Hydraulically or pneumatically operated rams may be provided automatically to move the inspection probes towards and away from the metallic object. Electronic signals generated by the inspection probes and representative of the condition of the surface under inspection may be processed in equipment similar or identical to that disclosed in our U.K. Pat. No. 1,475,517, or co-pending Application No. 2,008,259A.

The assembly may be suspended from a system of springs to facilitate movement of the assembly about the path of an object under inspection. In such an arrangement, tie bars are provided to inhibit movement of the assembly along the path taken by such an object.

According to the present invention in another aspect, there is provided a method of inspecting a corner of an elongate metallic object of generally rectangular or square cross-section in which an inspection probe carried by a scanning head is sited with respect to the corner to be inspected by moving rollers of a displaceable entry roller box rigid with the scanning head into contact with flat surfaces of the object as the object passes through the entry roller box.

Surface conditions detected by the inspection apparatus include surface defects, surface bruising and localised magnetic areas. The term "defect" as used herein is to be taken as including all such conditions.

The invention will now be described by way of example only, with reference to the accompanying diagrammatic drawings, in which.

Figure 1:
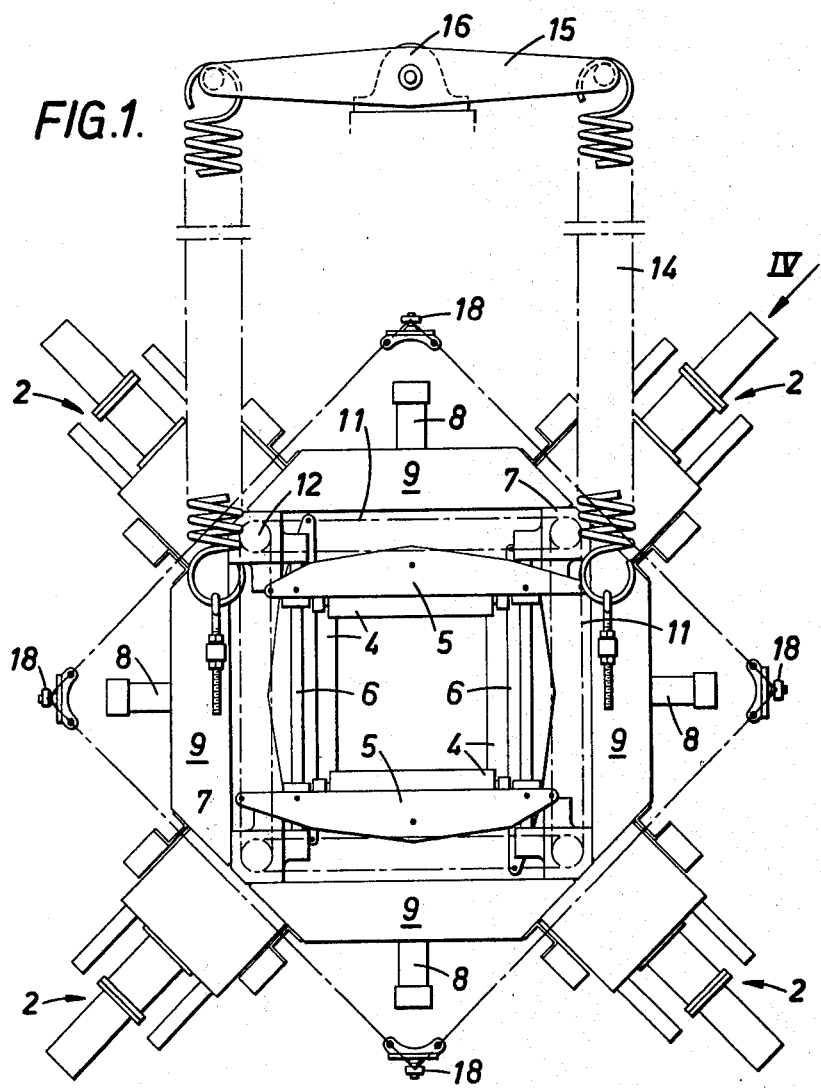
FIG. 1 is a front elevation of apparatus in accordance with the invention for inspecting the four corners of a metal billet.
Figure 2:
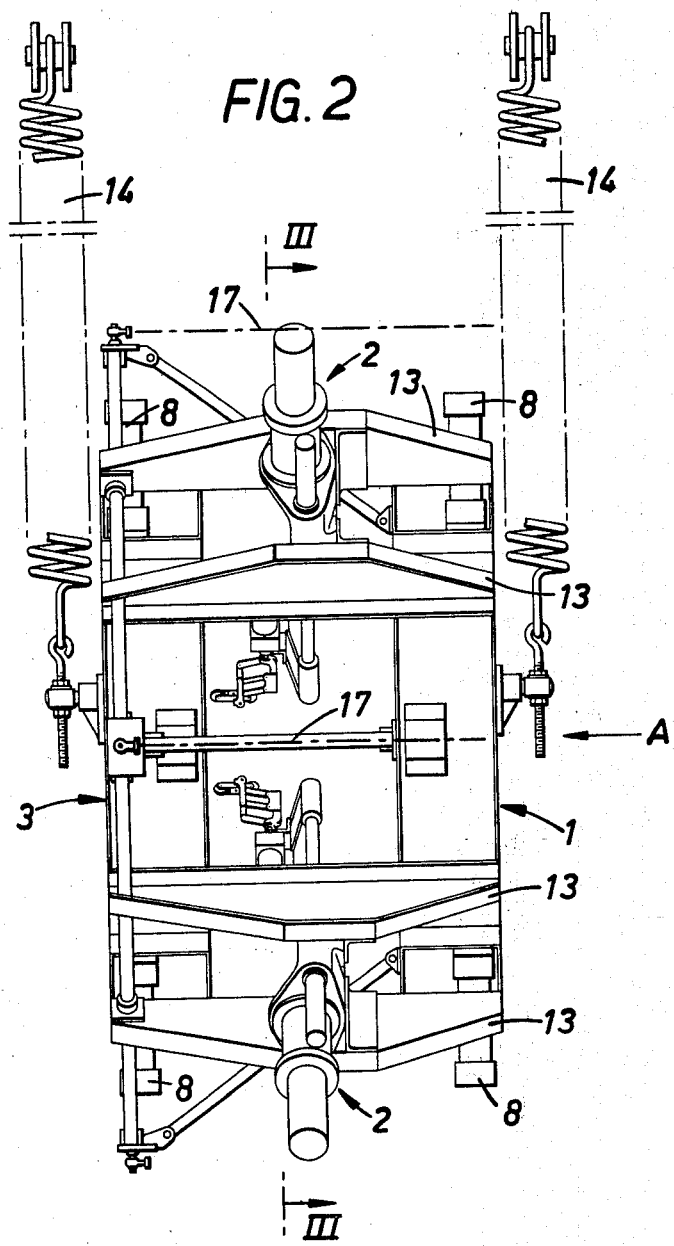
FIG. 2 is a side elevation of the apparatus shown in FIG. 1.

The apparatus illustrated in the drawings includes a rigid assembly of an entry roller box (1), four scanning heads (2) and an exit roller box (3). Each roller box (the exit roller box (3) being a mirror image of entry roller box (1)) comprises four rollers (4) each carried by a yoke (5) slidably-mounted between a pair of slideways (6) located between corner castings (7). The yokes can be moved along their respective slideways by pneumatic cylinders (8) mounted one on each of four trapezium-shaped cross members (9) which, together with the corner castings (7), define an annular housing for the yoke-mounted rollers (4). Opposite yokes (5) are each connected at their ends to endless chains (11) which track about sprockets (12) mounted on the corner castings (7) to synchronise movement and travel of the yokes and, consequently, the rollers (4). The entry and exit roller boxes (1) (3) are joined by four pairs of beams (13), each pair together providing a mounting for one of four scanning heads (2). The resulting rigid assembly of the roller boxes (1) (3) and the scanning heads (2) is suspended by a system of coil springs (14) from a balance beam (15) pivotably-mounted within a pivot block (16).

Four longitudinal tie rods (17), in line with the intended direction of movement of a billet through the apparatus, are provided to inhibit movement of the apparatus in this direction. The tie rods (17) have ball joints (18) at their ends to allow the rigid assembly of the roller boxes and the scanning heads to move upwardly, downwardly and to twist due to the action of a billet passing through the roller boxes.

Figure 3:
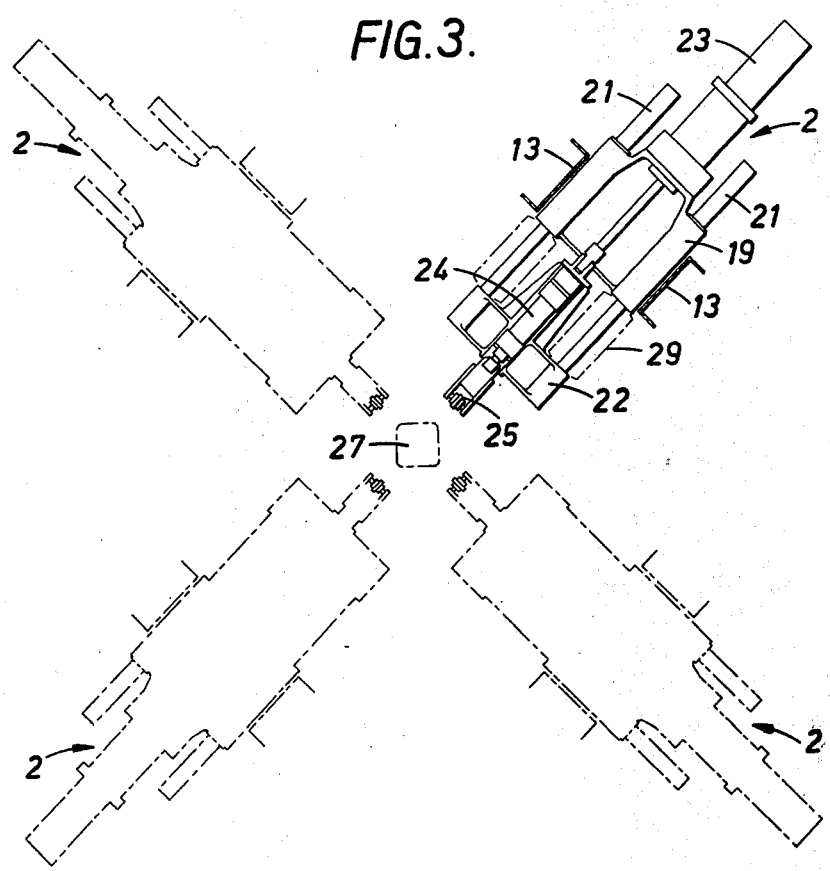
FIG. 3 is a section taken along line III—III of FIG. 2.
Figure 4:
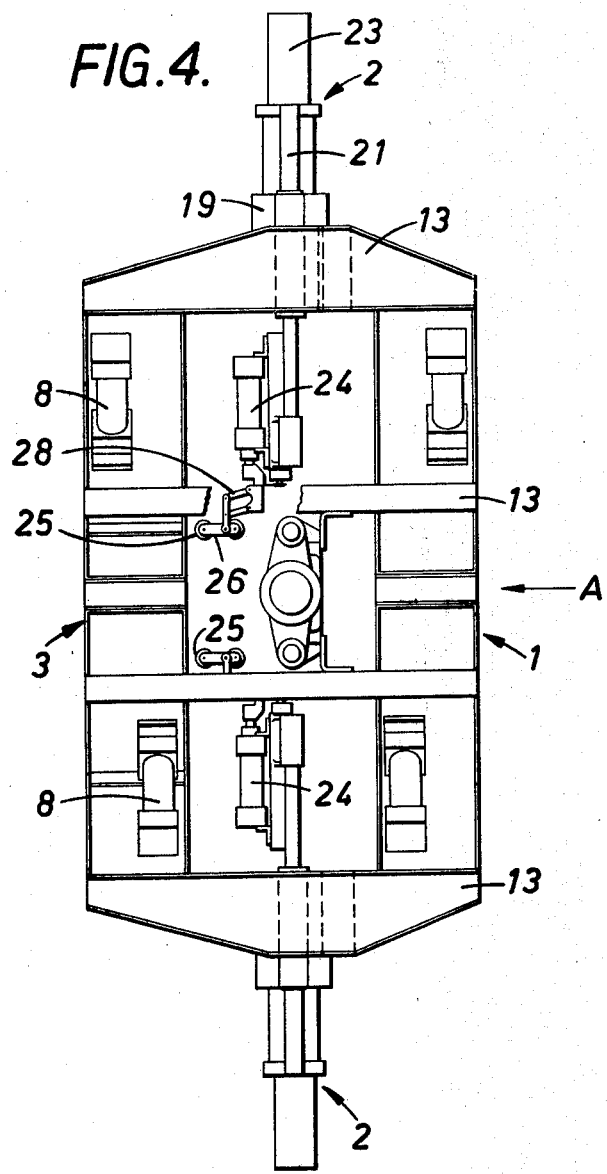
FIG. 4 is a side elevation taken in the direction of arrow IV—IV of FIG. 1.

The scanning heads (2) are mounted diagonally with respect to the roller boxes and are of identical construction, each comprising a slide bar casting (19) supported between one pair of the beams (13), (see FIG. 3). The casting (19) co-operates with two slide bars (21) which support a cross-head casting (22). A linear actuator (23) is operable to drive the cross-head casting (22) towards and away from the slide bar casting (19), the two slide bars (21) travelling within complementary bores formed within the casting (19). Mounted on the cross-head casting (22) is a pneumatic cylinder (24) operable to move a wheeled carriage (25) supporting an electronic probe (26) into engagement with the opposed corner of a billet (27) passing through the apparatus in the direction indicated by arrow "A". The carriage (25) is attached to the piston of the pneumatic cylinder (24) through a system of parallel links (28) which enable the carriage to move over irregularities in the surface of a billet under inspection. Each slide bar (21) is housed within a bellows cover (29).

The operation of the above-described apparatus will now be described. Prior to entry of a billet into the apparatus, and to satisfy changes in billet size, each wheeled carriage (25) is pre-positioned above the path to be taken by the respective corner to be inspected by the respective carriage-mounted probe. This is effected by operating the actuator which moves the cross-head casting towards and away from the billet path. The steel billet (27) travels along a roller table (not shown) and enters the entry roller box (1) generally centrally within the area defined by the four rollers (4). As the billet enters the box (1) a control mechanism is operated which actuates the pneumatic cylinders (8) to move the yoke-operated rollers (4) into engagement with the four sides of the billet. This movement is synchronised through the system of chains (11) whereby each roller travels through the same distance. Engagement of the side faces of the billet by the rollers automatically orientates the rigid assembly of the roller boxes and the scanning heads with respect to the billet so that the carriage-mounted electronic probes (26) are sited immediately above the four corners of the billet. After engagement of the side faces of the billet by the rollers, the pneumatic cylinders (24) are actuated to drive each carriage (25) into contact with the adjacent corner surface of the billet. As the billet enters the exit roller box (3) a similar control is activated to cause the four rollers of the exit roller box to be moved into engagement with the side faces of the billet as it leaves the apparatus. The spring-mounting of the rigid assembly of the roller boxes and the scanning heads permits upward, downward and twisting movement of the assembly so as to ensure that the scanning heads (2) are properly sited above the corners of the billet.

The electronic probes (26) are connected to transmit electronic signals representative of the condition of the corner surfaces under inspection, these signals being processed in equipment similar or identical to that disclosed and claimed in our U.K. Pat. No. 1,475,517, or co-pending Application No. 2,008,259A.

We claim:

1. Apparatus for inspecting a corner surface of an elongate metallic object of generally rectangular or square cross-section comprising; a rigid assembly having an entry roller box, the entry roller box comprising several rollers movable collectively into contact with flat surfaces of an object to be inspected as it enters the entry roller box to locate the assembly positively with respect to the object; a scanning head having a surface inspection probe, said scanning head supported for movement about the path to be taken by the object under inspection such that, when said rollers are moved into contact with the flat surfaces of said object, a surface inspection probe of the scanning head is sited opposite a corner of the object; and, spring means suspendingly supporting the assembly so as to facilitate movement of the assembly about the path of the object under inspection.

2. Apparatus as claimed in claim 1 wherein the rigid assembly additionally includes an exit roller box similarly comprising several rollers movable collectively into contact with flat surfaces of an object under inspection as it leaves the assembly through the exit box.

3. Apparatus as claimed in claim 1 or claim 2 wherein the said assembly carries a plurality scanning heads and of inspection probes collectively movable to positions immediately above the corners of an object under inspection.

4. Apparatus as claimed in any of claims 1 or 2 wherein ram is provided automatically to move the inspection probes towards and away from the metallic object.

5. Apparatus as claimed in claim 4 wherein tie bars are provided to inhibit movement of the assembly along the path taken by such an object.

6. A method of inspecting a corner of an elongate metallic object of generally rectangular or square cross-section in which a rigid assembly has an inspection probe carried by a scanning head to be sited with respect to the corner to be inspected comprising the steps of; moving rollers of a displaceable entry roller box rigid with the scanning head into contact with flat surfaces of the object so as to position the object as it passes through the entry roller box; and, supporting the assembly by a system of springs to facilitate movement of the assembly about the path of the object under inspection.

7. Apparatus as claimed in claim 3 wherein rams are provided automatically to move the inspection probes towards and away from the metallic object.

8. Apparatus as claimed in claims 1 or 2 wherein tie bars are provided to inhibit movement of the assembly along the path taken by such an object.

9. Apparatus as claimed in claim 3 wherein tie bars are provided to inhibit movement of the assembly along the path taken by such an object.

* * * * *